US00PP17395P2

(12) United States Plant Patent
Olbricht

(10) Patent No.: US PP17,395 P2
(45) Date of Patent: Jan. 30, 2007

(54) ***GERANIUM* PLANT NAMED 'REGVEL'**

(50) Latin Name: *Pelargonium grandiflorum*
Varietal Denomination: Regvel

(75) Inventor: Klaus Olbricht, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 35 days.

(21) Appl. No.: 11/151,841

(22) Filed: Jun. 14, 2005

(51) Int. Cl.
*A01H 5/00* (2006.01)

(52) U.S. Cl. ..... Plt./331
(58) Field of Classification Search ..... Plt./331
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of Regal *Geranium* plant named 'Regvel', characterized by its upright plant habit; vigorous growth habit; freely basal branching habit; and large red purple-colored flowers.

1 Drawing Sheet

Botanical designation: *Pelargonium grandiflorum.*
Cultivar denomination: 'Regvel'.

BACKGROUND OF THE INVENTION

The present invention relates to a new and distinct cultivar of Regal *Geranium* plant, botanically known as *Pelargonium grandiflorum,* and hereinafter referred to by the name 'Regvel'.

The new Regal *Geranium* is a product of a planned breeding program conducted by the Inventor in Dresden, Germany. The objective of the breeding program was to develop new Regal *Geraniums* that did not require a cooling treatment for flower development.

The new Regal *Geranium* originated from a cross-pollination made by the Inventor during 2001 of two unidentified proprietary selections of *Pelargonium grandiflorum,* not patented. The cultivar Regvel was discovered and selected by the Inventor as a flowering plant within the progeny from the stated cross-pollination in a controlled environment in Dresden, Germany in 2002.

Asexual reproduction of the new cultivar by terminal cuttings in a controlled environment in Dresden, Germany since 2002 has shown that the unique features of this new Regal *Geranium* are stable and reproduced true to type in successive generations of asexual reproduction.

SUMMARY OF THE INVENTION

The following traits have been repeatedly observed and are determined to be the unique characteristics of 'Regvel'. These characteristics in combination distinguish 'Regvel' as a new cultivar and distinguish it from other known Regal *Geranium* cultivars:

1. Upright plant habit.
2. Vigorous growth habit.
3. Freely basal branching habit.
4. Large red purple-colored flowers.
5. Does not require cooling treatment for flower development.

Plants of the new Regal *Geranium* differ primarily from plants of the parent selections in flower coloration.

Plants of the new Regal *Geranium* can be compared to plants of the cultivar Pacabla, disclosed in U.S. Plant Pat. No. 16,754. In side-by-side comparisons conducted in Dresden, Germany, plants of the new Regal *Geranium* differed from plants of the cultivar Pacabla in the following characteristics:

1. Plants of the new Regal *Geranium* had smaller umbels and flowers than plants of the cultivar Pacabla.
2. Plants of the new Regal *Geranium* had longer and more pubescent pedicels than plants of the cultivar Pacabla.
3. Plants of the new Regal *Geranium* and the cultivar Pacabla differed in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Regvel *Geranium*. The photograph comprises a side perspective view of a typical flowering plant of 'Regvel' grown in a container.

DETAILED BOTANICAL DESCRIPTION

Plants of the cultivar Regal have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in 13-cm containers in Dresden, Germany, and under commercial practice in a glass-covered greenhouse with day temperatures about 18° C., night temperatures about 16° C. and light levels less than 60,000 lux. Plants used for the photograph and the description were about six months old. In the following description, color references are made to The Royal Horticultural Society Colour Chart, 1995 Edition, except where general terms of ordinary dictionary significance are used.

Botanical classification: *Pelargonium grandiflorum* cultivar Regvel.

Parentage:

*Female, or seed, parent.*—Unidentified proprietary selection of *Pelargonium grandiflorum,* not patented.

*Male, or pollen, parent.*—Unidentified proprietary selection of *Pelargonium grandiflorum,* not patented.

Propagation:

*Type cutting.*—Terminal cuttings.

*Time to initiate roots.*—Summer: About 12 days at 23° C. Winter: About 14 days at 23° C.

*Time to produce a rooted young plant.*—Summer: About 30 days at 23° C. Winter: About 32 days at 23° C.

*Root description.*—Fine, fibrous; white in color.

*Rooting habit.*—Freely branching, moderately dense.

Plant description:

*General appearance.*—Upright plant habit; uniformly mounded; inverted triangle; densely foliated.

*Growth and branching habit.*—Vigorous growth habit. Freely basal branching habit with about eight lateral branches per plant.

*Plant height, to top of umbels.*—About 30 cm.

*Plants height, to top of foliar plane.*—About 22 cm.

*Plant width.*—About 30 cm.

*Lateral branches.*—Length: About 15 cm. Diameter: About 8 mm. Internode length: About 1 to 2 cm. Texture: Pubescent. Color: 144A.

*Foliage description.*—Arrangement: Alternate or opposite; simple. Length: About 6 cm. Width: About 8 cm. Shape: Cordate; palmately lobed. Apex: Acute. Base: Cordate; open. Margin: Serrate to biserrate. Venation pattern: Palmate. Texture, upper and lower surfaces: Slightly pubescent; leathery. Color: Developing and fully expanded foliage, upper surface: 137B; venation, 137B. Developing and fully expanded foliage, lower surface: 137C; venation, 143C. Petiole: Length: About 6 cm. Diameter: About 3 mm. Texture, upper and lower surfaces: Pubescent. Color, upper and lower surfaces: 144A.

Flower description:

*Flower arrangement.*—Rotate flowers arranged in rounded hemispherical umbels arising from apical leaf axils. Umbels displayed above the foliage on strong peduncles and flowers on strong pedicels. Flowers face upright to outwardly. Flowers not persistent. Flowers not fragrant.

*Quantity of flowers.*—About ten umbels per plant each umbel with about four to six flower buds and open flowers.

*Flowering season.*—Year-round under greenhouse conditions. In the garden in Dresden, Germany, flowering is continuous during the spring and summer. Plants do not require a cooling treatment for flower development.

*Flower longevity.*—Individual flowers last about one week on the plant.

*Umbel height.*—About 5 to 6 cm. Umbel diameter: About 8 cm. Flower diameter: About 4 cm. Flower depth (height): About 3 to 4 cm. Flower buds: Length: About 2.5 cm. Diameter: About 8 mm. Shape: Elliptic. Color: Darker than 59A. Petals: Quantity per flower: About five to seven. Length: About 3.5 cm. Width: About 2 to 3 cm. Shape: Oval to obovate. Apex: Rounded. Base: Cuneate. Margin: Entire. Texture, upper and lower surfaces: Smooth, glabrous; satiny. Color: When opening and fully opened, upper surface: Darker than 59A; towards the margin, 46A; towards the base, 67A; venation, darker than 59A; color becoming closer to 46A with development. When opening and fully opened, lower surface: 53A; towards the base; 67A; venation, darker than 59A.

*Sepals.*—Quantity per flower: Five, arranged in a single whorl. Length: About 1.5 cm. Width: About 5 mm. Shape: Lanceolate. Apex: Acute. Base: Attenuate. Margin: Entire. Texture, upper and lower surfaces: Pubescent. Color, upper and lower surfaces: 146C.

*Peduncle* (*umbel stem*).—Length: About 6 cm. Diameter: About 3 mm. Strength: Strong. Texture: Pubescent. Color: 146B.

*Pedicel* (*individual flower stem*).—Length: About 3 cm. Diameter: About 1.5 mm. Strength: Strong. Texture: Pubescent. Color: 146B.

*Reproductive organs.*—Androecium: Stamen quantity per flower: About ten. Anther shape: Elliptic. Anther color: 73B. Pollen amount: Abundant. Pollen color: Orange. Gynoecium: Pistil quantity per flower: One. Pistil length: About 1.7 cm. Stigma shape: Five-parted. Stigma color: Darker than 59A. Style length: About 1 cm. Style color: Darker than 59A. Ovary color: 146C.

*Seed.*—Length: About 2 to 3 mm. Diameter: About 1 mm. Shape: Elliptic. Color: Brown.

Disease/pest resistance: Plants of the new Regal *Geranium* have not been observed to be resistant to pathogens and pests common to Regal *Geraniums*.

Garden performance: Plants of the new Regal *Geranium* have been observed to tolerate rain, wind, and temperatures ranging from 10 to 25° C.

It is claimed:

1. A new and distinct cultivar of Regal *Geranium* plant named 'Regvel', as herein illustrated and described.

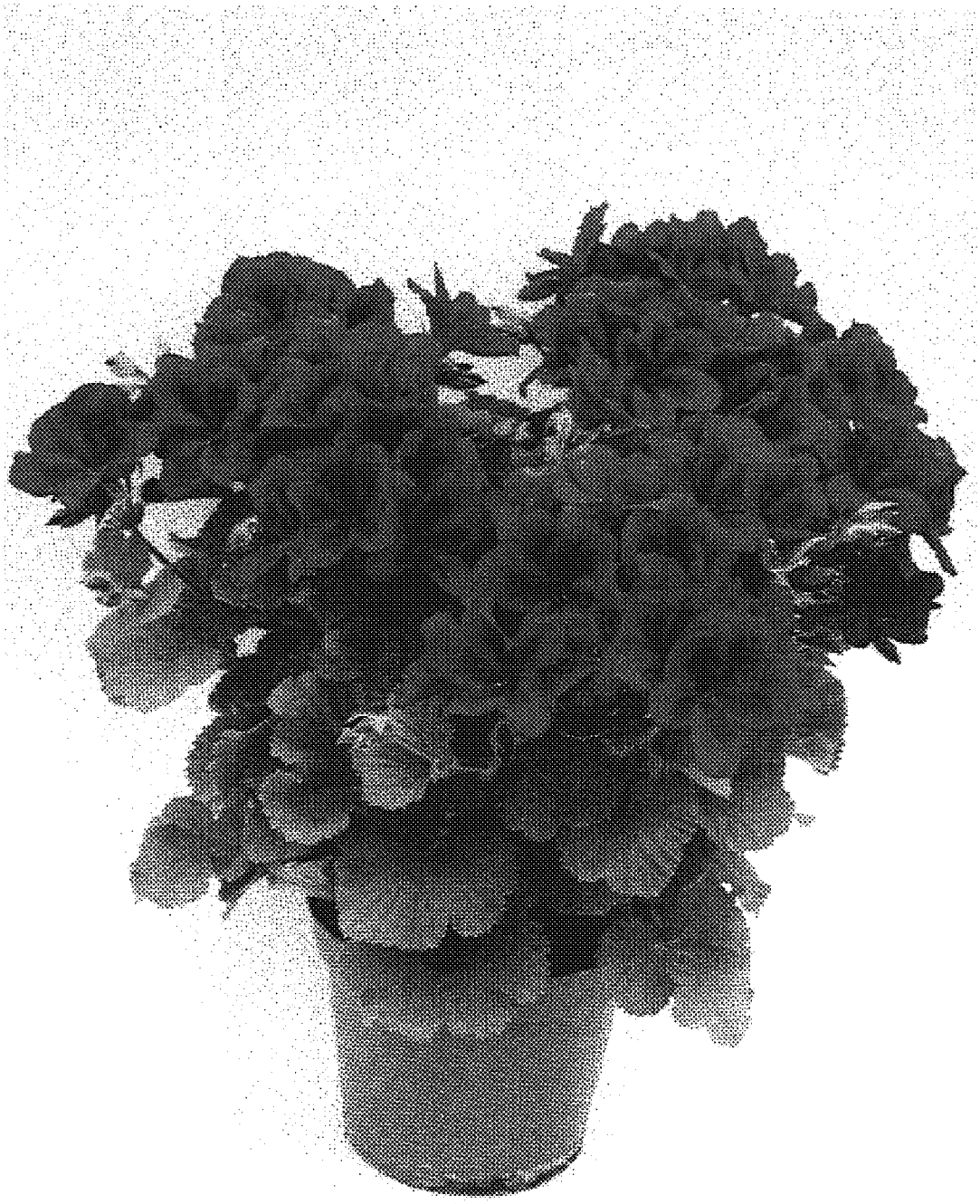

* * * * *